United States Patent [19]

Tanaka et al.

[11] Patent Number: 5,762,913
[45] Date of Patent: Jun. 9, 1998

[54] PHOTOCHROMIC COMPOUND OXIDE AND COSMETIC COMPRISING THE SAME

[75] Inventors: Hirokazu Tanaka; Akira Nakao; Takumi Miyazaki, all of Kitakyushu, Japan

[73] Assignee: Catalysss & Chemicals Industries Co., Ltd., Tokyo, Japan

[21] Appl. No.: 448,426

[22] PCT Filed: Jan. 24, 1995

[86] PCT No.: PCT/JP95/00076

§ 371 Date: Jun. 5, 1995

§ 102(e) Date: Jun. 5, 1995

[87] PCT Pub. No.: WO95/20184

PCT Pub. Date: Jul. 27, 1995

[30] Foreign Application Priority Data

Jan. 24, 1994 [JP] Japan ................................ 6-5629

[51] Int. Cl.⁶ ............................ A61K 7/42; C01G 23/047; C09C 1/36
[52] U.S. Cl. .......................... 424/59; 106/286.4; 106/437; 252/309; 252/313.1; 423/612; 424/60; 424/400; 424/401
[58] Field of Search ................... 424/59, 60, 400, 424/401; 252/309, 313.1; 423/612; 106/437, 286.4

[56] References Cited

U.S. PATENT DOCUMENTS

| 5,176,905 | 1/1993 | Ohno et al. | 424/69 |
| 5,403,513 | 4/1995 | Sato et al. | 252/309 |

FOREIGN PATENT DOCUMENTS

| 0359909 | 3/1990 | European Pat. Off. | A61K 7/42 |
| 0526712 | 2/1993 | European Pat. Off. | A61K 7/42 |
| 0624553 | 11/1994 | European Pat. Off. | |
| 50-133998 | 10/1975 | Japan | |
| 63-132811 | 6/1988 | Japan | |
| 6345433 | 12/1994 | Japan | |

*Primary Examiner*—Shelley A. Dodson
*Attorney, Agent, or Firm*—Webb Ziesenheim Bruening Logsdon Orkin & Hanson, P.C.

[57] ABSTRACT

The present invention provides a photochromic compound oxide of Ti, Fe and Si which may contain Al and a cosmetic comprising the above photochromic compound oxide which, even when a light quantity change instantaneously occurs as in taking a photographic picture with the use of flashlight, exhibits satisfactory changes in lightness and color difference in accordance with the above instantaneous light quantity change.

15 Claims, 6 Drawing Sheets

PHOTOCHROMIC COMPOUND OXIDE AND COSMETIC COMPRISING THE SAME

TECHNICAL FIELD

The present invention relates to a highly sensitive photochromic compound oxide and a cosmetic comprising the photochromic compound oxide.

BACKGROUND ART

Attempts have been made at blending a photochromic titanium oxide or a photochromic titanium oxide containing a metal such as Fe, Cr, Al, Mn, Cu, Ni, W or V in a cosmetic such as foundation.

For example, a photochromic composition capable of regulating color rendering properties which contains a member selected from among the above photochromic titanium oxides is described in International Publication WO 89/12084.

Japanese Patent Laid-open Publication No. 3(1991)-173810 describes photochromic flesh colored pigments each comprising a member selected from among the above photochromic titanium oxides. Japanese Patent Laid-open Publication No. 4(1992)-364117 describes photochromic ultraviolet ray shield powders each comprising a member selected from among the above photochromic titanium oxides.

For use in a cosmetic of flesh color as a basic tone, such as foundation, it is desired that:

(1) the photochromic titanium oxide exhibits a color darkening by irradiation of light;

(2) the photochromic titanium oxide has high photochromism sensitivity and undergo a tone change in accordance with a difference in light intensity between indoors and outdoors, i.e., a light intensity difference between the sunlight and the indoor light, so that the flesh color or color rendering can be held constant; and (3) the photochromic titanium oxide is safe for the human body.

From these viewpoints, a photochromic titanium oxide containing Fe is preferred and, especially, a photochromic titanium oxide containing only Fe as a photochromic flesh colored pigment has been brought into practical use. Incidentally, this photochromic titanium oxide containing only Fe is employed in all the Examples of the above-mentioned publications.

However, a cosmetic having, blended therein, this photochromic titanium oxide containing only Fe has a drawback in that, when a light quantity change instantaneously occurs as in taking a photographic picture with the use of flashlight, it cannot exhibit satisfactory changes in lightness and color difference in accordance with the above instantaneous light quantity change.

Thus, when photographed indoors with the use of flashlight, a woman's face made up with the cosmetic having, blended therein, the photochromic titanium oxide containing only Fe looks white and stands out in the photograph because of the delay of the color change of the titanium oxide.

The inventors have made extensive and intensive studies on the photochromic compound oxide containing Ti as a main component with a view toward overcoming the above drawback of the prior art. As a result, it has been found that a highly sensitive photochromic compound oxide which is unexpectable from the conventional photochromic compound oxide containing only Fe can be obtained by forming

2 a compound oxide by adding not only Ti and Fe but also Si optionally together with Al, and that, when a woman's face made up with a cosmetic having this compound oxide blended therein is photographed in colors indoors with the use of flashlight, a color picture can be obtained in which the woman's face holds its natural flesh color. The present invention has been completed on the basis of the above findings.

OBJECT OF THE INVENTION

As apparent from the foregoing, the object of the present invention is to provide a photochromic compound oxide which, even when a light quantity change instantaneously occurs as in taking a photographic picture with the use of flashlight, exhibits satisfactory changes in lightness and color difference in accordance with the above instantaneous light quantity change, and also to provide a cosmetic comprising this photochromic compound oxide.

DISCLOSURE OF THE INVENTION

The photochromic compound oxide of the present invention is a compound oxide of Ti, Fe and Si which may contain Al. In particular, a photochromic compound oxide is preferred in which Fe is contained in an amount of 0.05 to 10% by weight in terms of $Fe_2O_3$, Si is contained in an amount of 1 to 80% by weight in terms of $SiO_2$, and Al is contained in an amount of 0 to 30% by weight in terms of $Al_2O_3$. Further, it is preferred that the total content of Fe, Si and Al be not greater than 84% by weight in terms of the above oxides thereof.

Moreover, the cosmetic of the present invention comprises the above photochromic compound oxide of the present invention.

BRIEF DESCRIPTION OF THE DRAWINGS

A: Sample A, B: Sample B, C: Sample C and D: Sample D.

BEST MODE FOR CARRYING OUT THE INVENTION

The photochromic compound oxide and the cosmetic according to the present invention will now be described in greater detail.

A. Photochromic compound oxide

The photochromic compound oxide of the present invention is a compound oxide of Ti, Fe and Si which may contain Al, and which contains titanium oxide as a main component.

Although the titanium oxide may be selected from among anatase, rutile and amorphous titanium oxides and mixtures thereof, anatase titanium oxide and a titanium oxide mixture composed mainly of anatase titanium oxide are preferred. That is, the titanium oxide preferably contained as a main component in the photochromic compound oxide of the present invention possesses the properties of the anatase titanium oxide and may contain rutile titanium oxide and/or amorphous titanium oxide as long as the addition thereof is not detrimental to the above properties.

The photochromic compound oxide of the present invention has high sensitivity in photochromism and, even when a light quantity change instantaneously occurs as in taking a photographic picture with the use of flashlight, undergoes a rapid color darkening in accordance with the above instantaneous light quantity change, followed by the restoration of the dark color to the original color.

Also, the photochromic compound oxide of the present invention has the property of effectively absorbing ultraviolet.

In the photochromic compound oxide of the present invention, it is preferred that Fe be contained in an amount of 0.05 to 10% by weight, especially 0.1 to 8% by weight in terms of $Fe_2O_3$, that Si be contained in an amount of 1 to 80% by weight, especially not greater than 75% by weight and still especially not greater than 20% by weight in terms of $SiO_2$, and that Al be contained in an amount of 0 to 30% by weight, preferably 2 to 15% by weight in terms of $Al_2O_3$.

In the present invention, it is preferred that the total content of Fe, Si and Al be not greater than 84% by weight, especially not greater than 60% by weight in terms of the above oxides thereof.

The photochromic compound oxide of the present invention may be obtained by the process such as:

process (a) in which predetermined amounts of Fe, Si and Al compounds are uniformly mixed in particulate titanium oxide by mixing, etc. and subsequently the resultant particulate titanium oxide having, mixed therein, Fe, Si and Al compounds is calcined, or process (b) in which a titanium-oxide-base compound oxide sol containing Fe, Si and Al is prepared in accordance with the "process for producing a titanium oxide sol" described in Japanese Patent Laid-open Publication No. 63(1988)-229139, dried and calcined.

In both of the processes, the calcining temperature is generally 800° C. or higher, preferably in the range of 1000° to 1300° C..

Even when the photochromic compound oxide of the present invention is produced via the above calcining step conducted at such high temperatures, the titanium oxide contained as a main component in the photochromic compound oxide generally holds its anatase crystal structure without dislocation to a rutile titanium oxide.

Although the photochromic compound oxide of the present invention obtained by any of the above processes is generally used in a powdery form, its form is not particularly limited.

The average particle size of the photochromic compound oxide is generally 20 μm or less, preferably in the range of 0.05 to 0.5 μm.

The preparation of the titanium-oxide-base compound oxide sol containing Fe, Si and Al according to the above process (b) will further be described below in greater detail.

First, a mixed gel or sol of hydrated titanium oxide, hydrated iron oxide and hydrated aluminum oxide or a coprecipitated gel or sol therefrom are prepared. The above mixed gel may be obtained by mixing together hydrated titanium oxide, hydrated iron oxide and hydrated aluminum oxide gels respectively obtained by hydrolyses of an aqueous solution of a titanium salt such as titanium chloride or titanyl sulfate, an aqueous solution of an iron salt such as iron chloride and an aqueous solution of an aluminum salt such as aluminum chloride. Alternatively, the above mixed gel may be obtained by first preparing a hydrated titanium oxide gel, then adding an aqueous solution of an iron salt and an aqueous solution of an aluminum salt thereto and conducting hydrolysis thereof.

The coprecipitated gel of hydrated titanium oxide, hydrated iron oxide and hydrated aluminum oxide may be obtained by conducting hydrolysis of an aqueous solution of a mixture of titanium, iron and aluminum salts. Peptization of these mixed gel and coprecipitated gel with an acid gives sols. These mixed gel or sol and coprecipitated gel or sol may be prepared by the conventional processes such as one in which titanium, iron and aluminum alkoxides are hydrolyzed in place of the above described processes. The "hydrated titanium oxide", "hydrated iron oxide" and "hydrated aluminum oxide" used herein are generic terminologies respectively meaning titanium oxide hydrate together with titanium hydroxide, iron oxide hydrate together with iron hydroxide and aluminum oxide hydrate together with aluminum hydroxide.

Subsequently, hydrogen peroxide is added to the above mixed gel or sol or coprecipitated gel or sol, thereby dissolving the hydrated titanium, hydrated iron and hydrated aluminum oxides so that a homogeneous aqueous solution thereof is obtained. The amount of added hydrogen peroxide is preferably not less than 1.5 in terms of $H_2O_2/(TiO_2+Fe_2O_3+Al_2O_3)$ (weight ratio). When hydrogen peroxide is added in the above amount, the hydrated titanium, hydrated iron and hydrated aluminum oxides can be completely dissolved. When the total concentration of the hydrated titanium, hydrated iron and hydrated aluminum oxides is too high in the aqueous solution, not only does the dissolution take a long time but also undissolved material may be precipitated or the aqueous solution may become too viscous. Therefore, the total concentration of the hydrated titanium, hydrated iron and hydrated aluminum oxides in the aqueous solution is preferred to be about 6% by weight or less, especially about 4% by weight or less in terms of $(TiO_2+Fe_2O_3+Al_2O_3)$.

A silicon compound, e.g., an alkali silicate, silica gel or silicic acid solution is mixed into the thus obtained hydrogen-peroxide-dissolving aqueous solution and heated at 80° C. or higher. Thus, a sol having a particulate compound oxide of Ti, Fe, Al and Si dispersed therein is obtained.

The method for the above mixing of the silicon compound into the hydrogen-peroxide-dissolving aqueous solution is not particularly limited. For example, the entire predetermined amounts of the above aqueous solution and the silicon compound may be mixed together at once. Alternatively, the above aqueous solution may be mixed with part of the silicon compound and heated, followed by addition of the balance of the silicon compound in accordance with the advance of the reaction.

Also, the desired sol having a particulate compound oxide of Ti, Fe, Al and Si dispersed therein can be obtained by adding the above silicon compound to the above mixed gel or sol or coprecipitated gel or sol, then adding hydrogen peroxide to the mixture to thereby dissolve the mixture and heating at 80° C. or higher. Further, the desired sol having a particulate compound oxide of Ti, Fe, Al and Si dispersed therein may be obtained by adding the silicon compound during the above preparation of the mixed gel or sol or coprecipitated gel or sol, then adding hydrogen peroxide to the resultant mixed gel or sol or coprecipitated gel or sol to thereby dissolve the gel or sol and heating at 80° C. or higher.

The particulate compound oxide of the present invention is required to contain Ti, Fe and Si in the compound oxide, but is not always needed to contain Al.

The particulate compound oxide not containing Al may be produced, for example, by the same processes as described above except that the above mixed gel or sol or coprecipitated gel or sol is prepared without the addition of an aqueous solution of an aluminum salt.

B. Cosmetic

The cosmetic of the present invention comprises the above photochromic compound oxide of the present invention.

The content of the photochromic compound oxide in the cosmetic is preferred to range from 1 to 30% by weight based on the total weight of the cosmetic. When the content is less than 1% by weight, depending on the cosmetic, there is the possibility that satisfactory lightness and color difference changes cannot be obtained in the exhibition of photochromism of the photochromic compound oxide contained in the cosmetic. On the other hand, when the content exceeds 30% by weight, it is likely for a color difference change to be so large as to give a sense of inharmoniousness.

The cosmetic of the present invention generally contains at least one member selected from among the various customary cosmetic ingredients, for example, oils such as higher aliphatic alcohols, higher fatty acids, ester oils, paraffin oils and waxes, alcohols such as ethyl alcohol, propylene glycol, sorbitol and glycols, humectants such as mucopolysaccharides, collagens, PCA salts and lactates, surfactants such as nonionic, cationic, anionic and amphoteric surfactants, thickeners such as gum arabic, xanthan gum, polyvinylpyrrolidone, ethylcellulose, carboxymethylcellulose, carboxyvinylpolymer and metamorphosed or unmetamorphosed clay minerals, solvents such as ethyl acetate, acetone and toluene, inorganic and organic pigments or dyes, antioxidants such as BHT and tocopherol, water, drugs, ultraviolet absorbents, pH buffers each composed of a salt of organic or inorganic acid, chelating agents, antiseptics and perfumes.

Further, if desired, the cosmetic of the present invention may contain at least one member selected from among inorganic fillers such as silica, talc, kaolin and mica and various organic resins.

In the production of the cosmetic of the present invention, generally, appropriate ingredients selected from among the above are directly blended. However, particles of the photochromic compound oxide of the present invention may be coated with, for example, an organic resin and then mixed with other ingredients.

The cosmetic of the present invention is used in various forms such as powdery, cake, pencil, stick, liquid, milky lotion and creamy forms.

EXAMPLES

The present invention will be illustrated below with reference to the following Examples, which should not be construed as limiting the scope of the invention.

Example 1

38.5 kg of an aqueous solution containing 2% by weight of titanium chloride in terms of $TiO_2$, 0.5 kg of an aqueous solution containing 2% by weight of iron chloride in terms of $Fe_2O_3$ and 4.0 kg of an aqueous solution containing 2% by weight of aluminum chloride in terms of $Al_2O_3$ were homogeneously mixed together, and aqueous ammonia was added until the pH value of the mixture became 8.5. Thus, a slurry was obtained, which was filtered and washed. 12 kg of a 35% aqueous hydrogen peroxide solution was added to thereby dissolve the slurry.

The thus obtained solution was diluted with pure water so as for the concentration of obtained compound oxide to become 1.0% by weight.

Subsequently, 3.5 kg of a silicic acid solution containing 4% by weight of silicic acid in terms of $SiO_2$ which was obtained by dealkalizing an aqueous solution of sodium silicate with a cation exchange resin was added to the above solution and heated at 200° C. for 20 hrs in an autoclave. Thus, a compound oxide sol was obtained.

The thus obtained compound oxide sol was dried, calcined at 1050° C. for 5 hrs and pulverized, thereby obtaining a compound oxide having an average particle size of 0.5 μm (sample A).

The composition and average particle size of the obtained compound oxide (sample A) are shown in Table 1.

Compound oxides (samples B, C and D) shown in Table 1 were obtained in the same manner as in the preparation of the sample A, except that the aqueous aluminum chloride solution was not employed and that the mixing ratio of the aqueous titanium chloride and iron chloride solutions and also the amount of added silicic acid solution were varied.

TABLE 1

| Sample | Composition (wt. %) | | | | Average particle size (μm) |
|---|---|---|---|---|---|
| | $TiO_2$ | $Fe_2O_3$ | $SiO_2$ | $Al_2O_3$ | |
| A | 77.0 | 1.0 | 14.0 | 8.0 | 0.5 |
| B | 93.0 | 0.3 | 6.5 | — | " |
| C | 86.8 | 0.8 | 12.4 | — | " |
| D | 43.4 | 0.4 | 56.2 | — | " |

The above samples A, B, C and D of powdery compound oxides were molded by compression molding, thereby obtaining measuring samples each having a diameter of 30 mm and a thickness of 5 mm.

Each of the measuring samples was irradiated with ultraviolet of 365 nm in wavelength, and the lightness change thereof was measured.

7

The measuring conditions were as follows.

An ultraviolet source capable of radiating ultraviolet of 365 nm in wavelength and each measuring sample were disposed at a spacing such that the intensity of ultraviolet on the surface of the measuring sample measured by the use of ultraviolet intensity meter (UM-1 manufactured by Minolta Co., Ltd.) was 3 mW/cm$^2$.

The measuring sample was allowed to stand still in a dark room at room temperature for 3 hrs prior to the irradiation of ultraviolet, and the surface of the measuring sample was irradiated with ultraviolet light from the ultraviolet source. The lightness (V) of the measuring sample was measured at ultraviolet irradiation periods of 1 min, 2 mins, 5 mins and 10 mins with the use of spectrophotometer (CM-2002 manufactured by Minolta Co., Ltd.).

Figure 1:
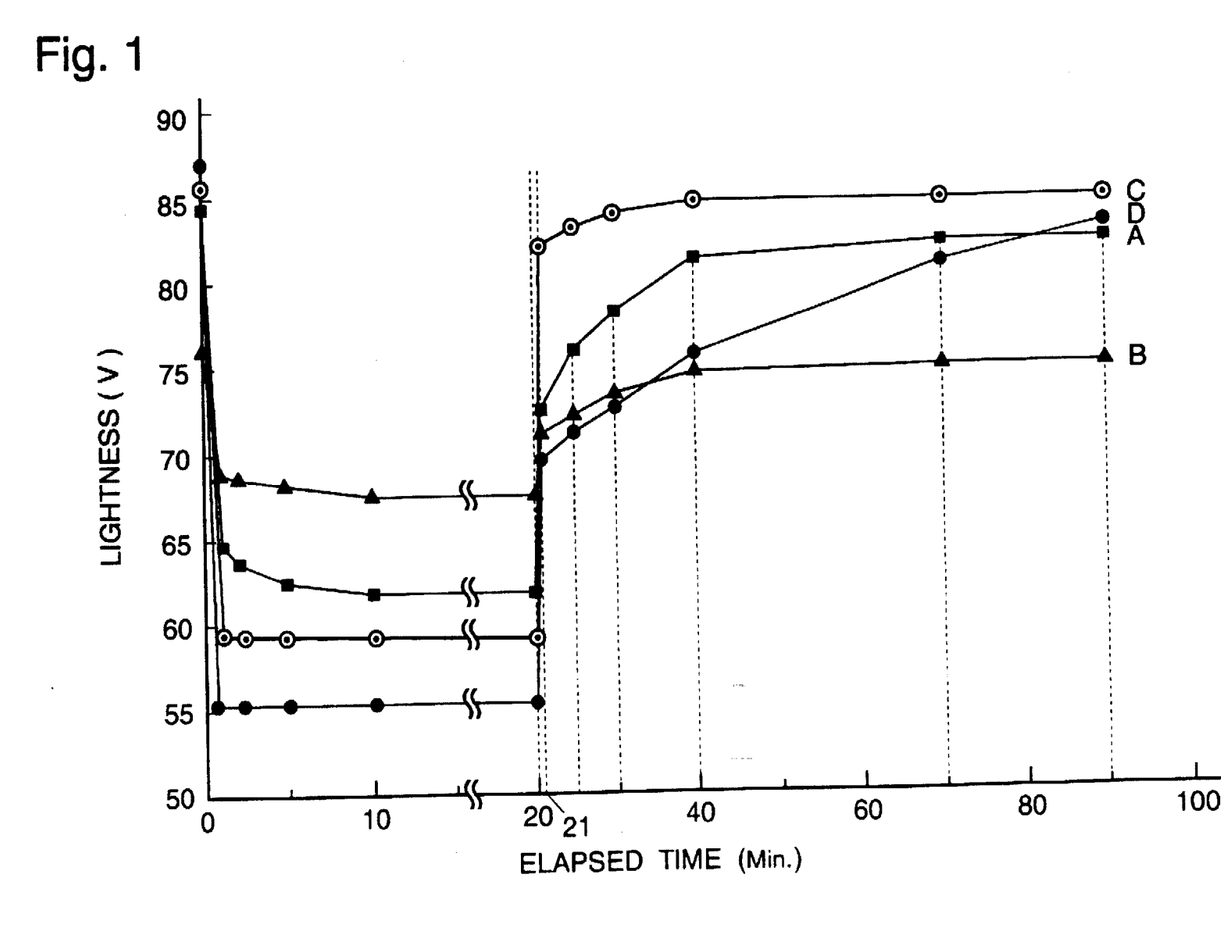
FIG. 1 is a graph showing the relationship between the duration of irradiation of ultraviolet to each photochromic compound oxide and the change of the lightness of the photochromic compound oxide and also showing the restoration of the lightness of the photochromic compound oxide which has occurred after the discontinuation of the irradiation of ultraviolet to the photochromic compound oxide.

The results are shown in FIG. 1.

FIG. 1 demonstrated that, with respect to all the measuring samples obtained from the samples A, B, C and D of powdery compound oxides, the lightness became constant when the surface thereof was irradiated with ultraviolet of 3 mw/cm$^2$ for 10 mins. In the figure, the lightness value at an elapsed time of 0 means a measurement obtained without the irradiation of ultraviolet immediately after the leaving of the measuring sample in the dark room for 3 hrs.

Further irradiation of the surface of each of the measuring samples with ultraviolet of 3 mW/cm$^2$ was conducted for 10 mins, i.e., the ultraviolet irradiation was conducted for a total of 20 mins. Then, the ultraviolet irradiation was discontinued, and the change of the lightness of each of the measuring samples with time was measured.

The results are jointly shown in FIG. 1.

As shown in FIG. 1, with respect to all the measuring samples obtained from the samples A, B, C and D of powdery compound oxides, the lightness was restored to 80 to 100% of that prior to the ultraviolet irradiaion in 20 mins after the discontinuation of the ultraviolet irradiation.

Example 2

Figure 2:
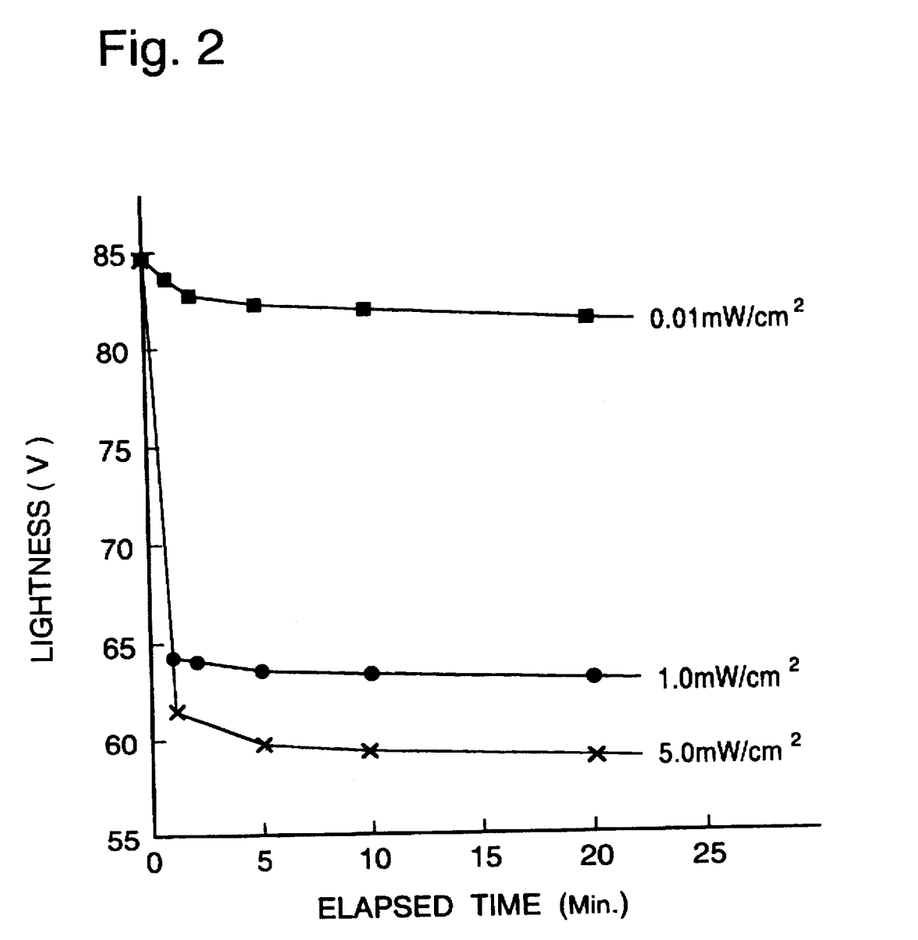
FIG. 2 is a graph showing the relationship between the duration of irradiation of ultraviolet to a photochromic compound oxide and the change of the lightness of the photochromic compound oxide which has been measured at varied intensities of ultraviolet irradiated to the photochromic compound oxide.

With respect to the measuring sample obtained by molding the sample A of powdery compound oxide, FIG. 2 shows the relationship between the duration of ultraviolet irradiation and the lightness of the measuring sample exhibited at varied ultraviolet irradiation intensities.

The ultraviolet irradiation intensity of 0.01 mW/cm$^2$ corresponds to the brightness in a room fluorescent lamp, the ultraviolet irradiation intensity of 1.0 mW/cm$^2$ corresponds to the brightness in the shade of a tree under the blue sky, and the ultraviolet irradiation intensity of 5.0 mW/cm$^2$ corresponds to the brightness in direct sunlight under the blue sky.

Example 3

Figure 3:
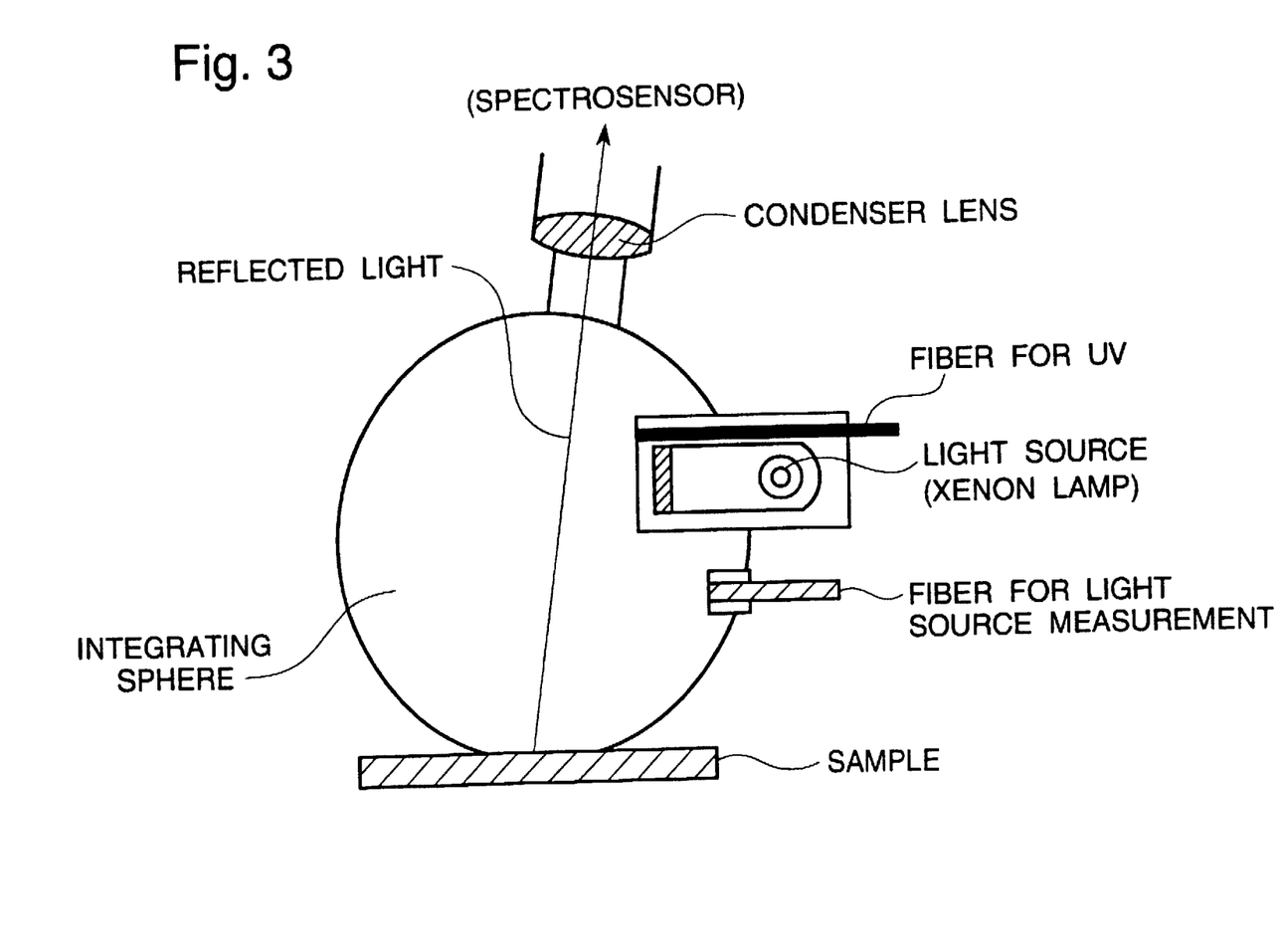
FIG. 3 is a schematic diagram of the construction of an apparatus suitable for use in measuring the lightness and color of a sample having just irradiated with ultraviolet instantaneously.

The lightness change of the sample A in accordance with an instantaneous light quantity change was measured by the use of the apparatus illustrated in FIG. 3.

The lightness change exhibited in accordance with the instantaneous light quantity change was also measured in the same manner as above with respect to a measuring sample (comparative sample) prepared from photochromic pigment (PHOTLIGHT-PKS produced by Shiseido Co., Ltd.) in the same manner as in Example 1.

The apparatus illustrated in FIG. 3 is a partial reconstruction of commercially available spectrophotometer (CM-2002 manufactured by Minolta Co., Ltd.). An optical fiber for introducing condensed ultraviolet rays emitted from an ultraviolet lamp is disposed in a cavity inside a housing in which a light source of the spectrophotometer is accommodated so that ultraviolet can be irradiated through a window of the light source toward the measuring sample. Thus, ultraviolet can be instantaneously irradiated from the front edge of the optical fiber toward the measuring sample, and the lightness change of the measuring sample immediately after the irradiation can be measured.

This measurement of the lightness change of the measuring sample was conducted in the following manner.

First, the measuring sample was allowed to stand still in a dark room for 3 hrs, and then the lightness thereof was measured.

Subsequently, ultraviolet of 365 nm in wavelength was irradiated from the front edge of the above optical fiber for 4 msec (1/250 sec), and immediately thereafter the lightness of the measuring sample was measured.

Further, the same ultraviolet was irradiated toward the measuring sample from the front edge of the optical fiber for 3 sec, and immediately thereafter the lightness of the measuring sample was measured.

Figure 4:
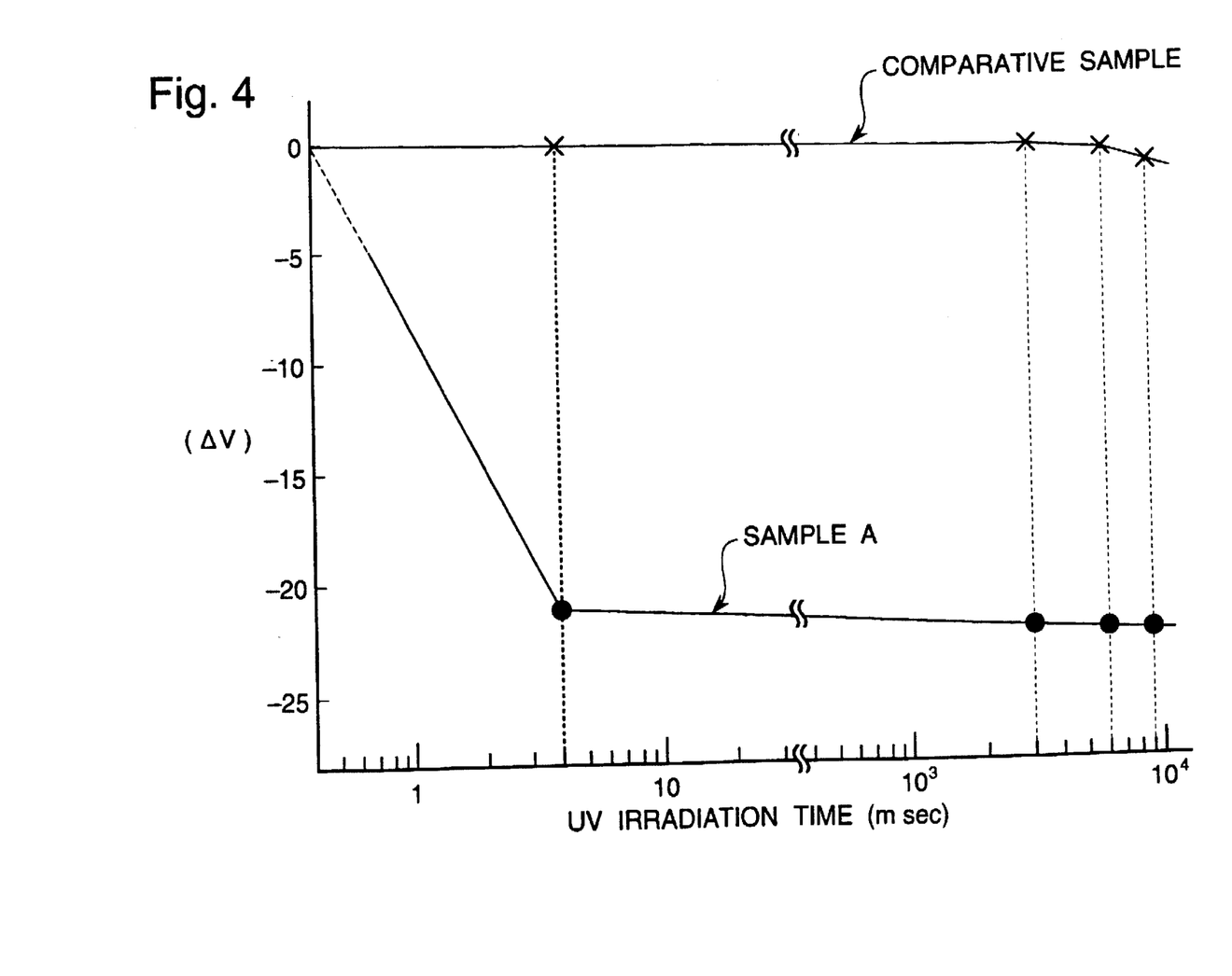
FIG. 4 is a graph showing an exemplary relationship of the difference between the lightness of a sample having just irradiated with ultraviolet instantaneously and that of the sample before the irradiation.

This operation was repeated. FIG. 4 is a graph showing the thus obtained relationship between the cumulative ultraviolet irradiation time and the lightness change of the measuring sample ($\Delta V$: difference between the lightness at the initial stage and the lightness immediately after the ultraviolet irradiation).

As shown in FIG. 4, the compound oxide of the present invention had a lightness change only by the irradiation of ultraviolet of 365 nm in wavelength for 4 msec, while the comparative sample did not show a lightness change by such irradiation and had a slight lightness change by irradiation of the same ultraviolet for a period as long as 6 sec.

Example 4

A foundation cake of the composition shown below was produced according to the customary procedure.

| | |
|---|---|
| photochromic compound oxide (sample A) | 15 wt. % |
| metallic soap | 5 |
| white pigment | 8 |
| particulate TiO$_2$ (particle size: 30 µm) | 7 |
| sericite | 40 |
| silica (SPHERON P-1500 produced by Catalysts & Chemicals Industries Co., Ltd.) | 5 |
| red pigment | 0.3 |
| yellow pigment | 0.4 |
| black pigment | 0.2 |
| talc | 8 |
| ester oil | 2 |
| ester wax | 1 |
| squalane | 2 |
| silicone oil | 6 |
| paraben | 0.2 |
| perfume | appropriate amount |

The color difference ($\Delta E$) of the above foundation cake by ultraviolet irradiation was measured by the use of spectrophotometer (CM-2002 manufactured by Minolta Co., Ltd.).

This measurement was carried out in the following manner.

First, the measuring sample was allowed to stand still in a dark room for 18 hrs, and then the color was measured.

Subsequently, ultraviolet of 365 nm in wavelength was irradiated so as for the ultraviolet intensity on the surface of the measuring sample to be 3 mW/cm² in the same manner as in Example 1. At irradiation periods of 1, 2, 5, 10 and 20 min, the colors of the measuring sample were measured, thereby determining the respective color differences (ΔE).

When the surface of the measuring sample was irradiated with the ultraviolet for a total of 20 mins, the irradiation of the ultraviolet was discontinued. The change with time of the color difference (ΔE) after the discontinuation of the ultraviolet irradiation was measured.

Figure 5:
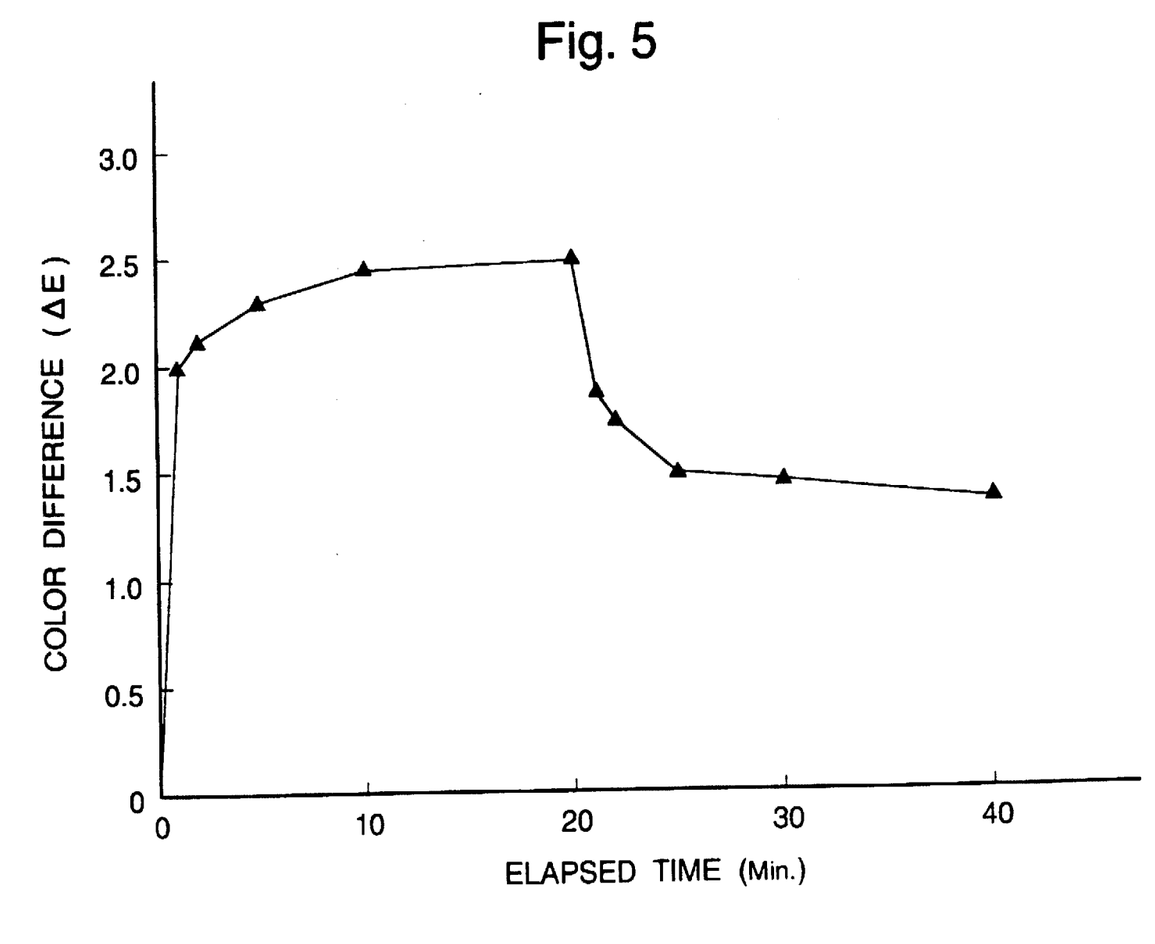
FIG. 5 is a graph showing an exemplary relationship between the duration of radiation of ultraviolet to a cosmetic comprising a photochromic compound oxide according to the present invention and the color difference of the cosmetic and also showing a relationship between the elapsed time after the discontinuation of the irradiation of ultraviolet to the cosmetic and the color difference of the cosmetic.

The results are shown in FIG. 5.

Example 5

Figure 6:
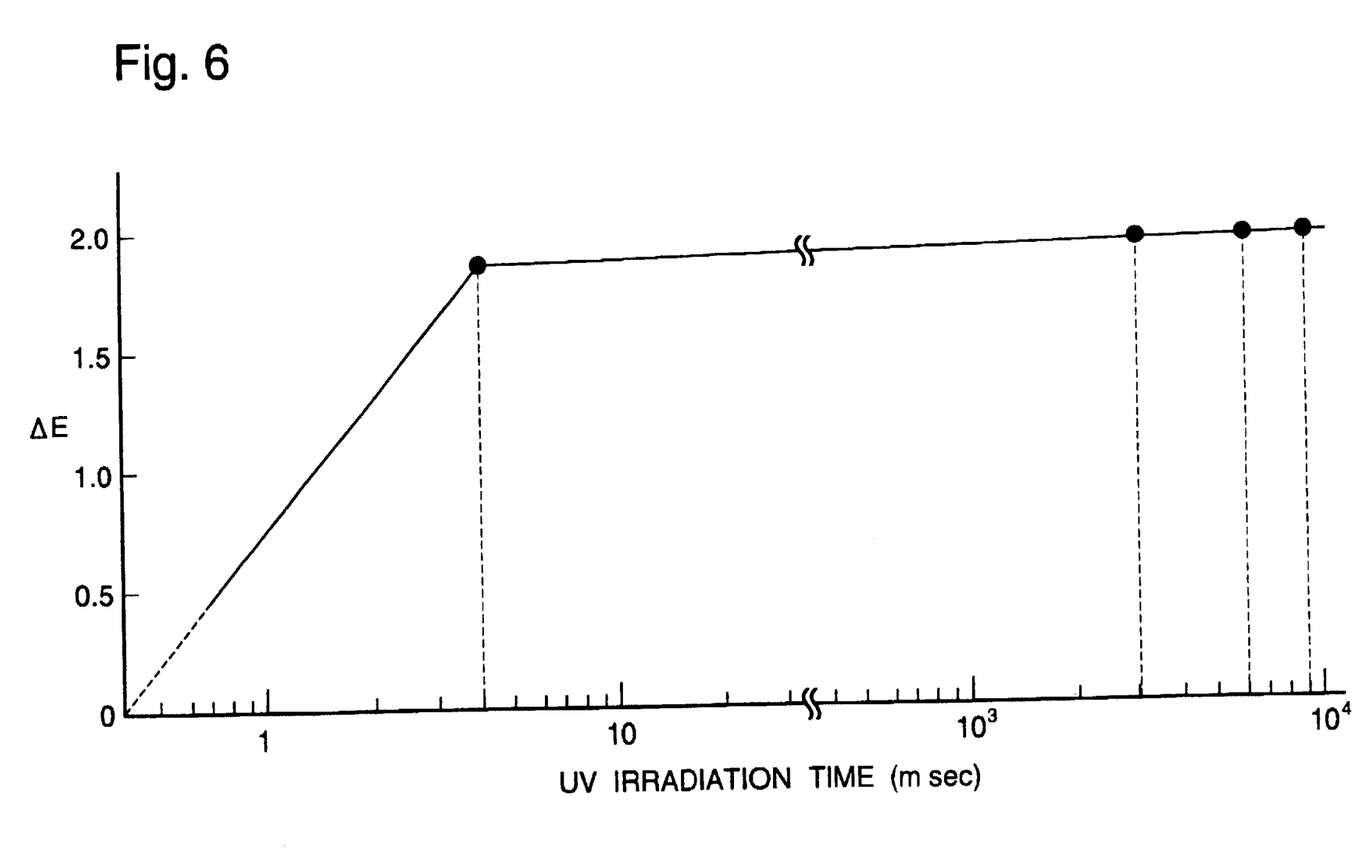
FIG. 6 is a graph showing an exemplary relationship of the color difference between a sample having just irradiated with ultraviolet instantaneously and that of the sample before the irradiation.

The change with time of the color difference (ΔE) immediately after the ultraviolet irradiation was measured under the same instantaneous light quantity change as in Example 3 with respect to the foundation cake obtained in Example 4. The results are shown in FIG. 6.

Moreover, the left half of a woman's face was made up with the foundation cake of Example 4 while the right half was made up with a commercially available foundation cake having no photochromism.

The woman's face was photographed with the use of flashlight in a dark room. The woman was asked to remain on standby in the dark room for 1 hr. Then, the woman's face was photographed in the natural light.

The two pictures were compared, and it was found that the left half of the woman's face made up with the foundation cake of Example 4, i.e., with a cosmetic of the present invention had substantially the same flesh color in the picture obtained by photographing in the dark room with the use of flashlight as in the picture obtained by photographing in the natural light, while the right half of the woman's face made up with the commercially available foundation cake having no photochromism looked white and stood out in the picture obtained by photographing in the dark room with the use of flashlight.

EFFECT OF THE INVENTION

The photochromic compound oxide of the present invention exhibits photochromism and is white or paleyellow in no irradiation while darkens its color by light irradiation.

The photochromic compound oxide of the present invention contains Ti, Fe, Si and optionally an appropriate amount of Al, has higher photochromism sensitivity, and exhibits much greater color change by ultraviolet irradiation and greater lightness difference and color difference than those of the photochromic titanium oxide containing only Fe which has been used as a photochromic pigment for cosmetic. That is, the photochromic compound oxide of the present invention corresponds to the conventional titanium oxide containing only Fe to which Si and optionally an appropriate amount of Al has been added, so that a marked improvement is attained in photochromic sensitivity as compared with that of the conventional photochromic titanium oxide containing only Fe.

Therefore, when a make-up is conducted with the cosmetic of the present invention comprising the above photochromic compound oxide, a picture in which the part made up has natural flesh color can be obtained by photographing indoors in colors with the use of flashlight.

Moreover, the photochromic compound oxide of the present invention has high ultraviolet absorbance.

Therefore, when a make-up is prepared with the cosmetic of the present invention comprising the above photochromic compound oxide, the skin made up is effectively protected from ultraviolet.

We claim:

1. A photochromic compound oxide comprising: 0.05–10% by weight, in terms of $Fe_2O_3$; 1–80% by weight, in terms of $SiO_2$ ; and balance of $TiO_2$.

2. The compound oxide as claimed in claim 1 comprising at least 16% by weight, in terms of $TiO_2$.

3. The compound oxide as claimed in claim 1 comprising 16–93% by weight, in terms of $TiO_2$.

4. The compound oxide as claimed in claim 1 further comprising up to 30% by weight, in terms of $Al_2O_3$.

5. The compound oxide as claimed in claim 4 comprising at least 16% by weight, in terms of $TiO_2$.

6. The compound oxide as claimed in claim 5, comprising 16–93% by weight, in terms of $TiO_2$.

7. The compound oxide as claimed in claim 5, comprising 16–77% by weight, in terms of $TiO_2$.

8. A cosmetic preparation comprising the photochromic oxide composition of claim 7.

9. The cosmetic preparation of claim 8 comprising 1 to 30% by weight said photochromic oxide composition.

10. A cosmetic preparation comprising the photochromic compound oxide of claim 4.

11. The cosmetic preparation as claimed in claim 10, comprising 1–30% by weight of said photochromic compound oxide.

12. A method of maintaining the natural flesh color of illuminated skin comprising the steps of a) applying a photochromic compound oxide comprising: 0.05–10% by weight in terms of $Fe_2O_3$; 1–80% by weight in terms of $SiO_2$: and balance of titanium oxide;

b) illuminating the skin with light; and c) allowing the color of said photochromic compound oxide to darken during exposure to the light; whereby the color of said photochromic compound oxide lightens upon extinguishment of the light.

13. The method of claim 12 wherein said photochromic compound oxide further comprises an oxide of Al.

14. The method of claim 13 wherein said photochromic compound oxide further comprises up to 30% by weight in terms of $Al_2O_3$.

15. The method of claim 12 wherein said step of illuminating the skin with light comprises instantaneously illuminating the skin with light.

* * * * *

UNITED STATES PATENT AND TRADEMARK OFFICE
CERTIFICATE OF CORRECTION

PATENT NO. : 5,762,913
DATED : June 9, 1998
INVENTOR(S) : Hirokazu Tanaka et al.

It is certified that error appears in the above-identified patent and that said Letters Patent is hereby corrected as shown below:

Title Page, [73] Assignee, "Catalysss" should read --Catalysts--.

Title Page, [57] ABSTRACT, line 4, "change" should read --changes--.

Title Page, [57] ABSTRACT, line 4, "occurs as" should read --as occurs--.

Column 3, Line 65 "1300°C.." should read --1300°C.--.

Claim 12 Column 10 Line 41 "$Fe_2O_{3:\ 1-80}$%" should read --$Fe_2O_3$; 1-80%--.

Claim 12 Column 10 Line 42 "$SiO_2$:" should read --$SiO_2$;--.

Signed and Sealed this

Twentieth Day of October, 1998

Attest:

BRUCE LEHMAN

*Attesting Officer*   *Commissioner of Patents and Trademarks*